US 11,432,833 B2

(12) United States Patent
Beverland (10) Patent No.: US 11,432,833 B2
(45) Date of Patent: Sep. 6, 2022

(54) SURGICAL KIT AND METHOD

(71) Applicant: DEPUY IRELAND UNLIMITED COMPANY, Ringaskiddy (IE)

(72) Inventor: David Beverland, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 34 days.

(21) Appl. No.: 16/973,519

(22) PCT Filed: Apr. 29, 2019

(86) PCT No.: PCT/EP2019/060894
§ 371 (c)(1),
(2) Date: Dec. 9, 2020

(87) PCT Pub. No.: WO2020/001830
PCT Pub. Date: Jan. 2, 2020

(65) Prior Publication Data
US 2021/0236145 A1 Aug. 5, 2021

(30) Foreign Application Priority Data

Jun. 26, 2018 (GB) .................................... 1810480
Mar. 27, 2019 (GB) .................................... 1904257

(51) Int. Cl.
*A61B 17/17* (2006.01)
(52) U.S. Cl.
CPC .................................. *A61B 17/175* (2013.01)
(58) Field of Classification Search
CPC ... A61B 17/15; A61B 2090/061; A61B 90/06; A61B 17/742
See application file for complete search history.

(56) References Cited

U.S. PATENT DOCUMENTS 4,621,630 A 11/1986 Kenna
4,959,066 A 9/1990 Dunn et al.
(Continued)

FOREIGN PATENT DOCUMENTS

| AU | 2006200152 A1 | 8/2006 |
| EP | 1797834 A1 | 6/2007 |
| TW | 201540251 A | 11/2015 |
| WO | 2002/026145 A1 | 4/2002 |
| WO | 2003/009170 A1 | 1/2003 |

(Continued)

OTHER PUBLICATIONS

WO International Search Report application No. PCT/EP2019/060976, dated Jul. 8, 2019.
(Continued)

*Primary Examiner* — Samuel S Hanna
(74) *Attorney, Agent, or Firm* — Cynthia K. Barnett (57) ABSTRACT

A surgical kit and method for performing a controlled resection of the neck of a femur during a hip replacement procedure. The kit includes a mounting portion. The mounting portion includes guide holes for inserting guide pins into the femoral head while the mounting portion is located on an anterior aspect of the femoral head. The kit also includes a body portion connected to the mounting portion. The body portion includes an opening for mounting the body portion on an intramedullary pin. The kit also includes a resection guide including guide holes having the same layout as the guide holes of the mounting portion, to allow the resection guide to be mounted on the anterior aspect of the femoral head with the guide pins inserted into the femoral head for positioning a resection plane indicator of the resection guide with respect to the neck of the femur.

10 Claims, 5 Drawing Sheets

(56) References Cited

U.S. PATENT DOCUMENTS

| | | | |
|---|---|---|---|
| 5,464,406 A | 11/1995 | Ritter et al. | |
| 5,578,037 A | 11/1996 | Sanders | |
| 5,607,431 A | 3/1997 | Dudasik et al. | |
| 6,258,097 B1 | 7/2001 | Cook et al. | |
| 6,421,630 B1 | 7/2002 | Yamada et al. | |
| 6,503,255 B1 * | 1/2003 | Albrektsson | A61B 17/15 606/89 |
| 7,582,091 B2 | 9/2009 | Duncan et al. | |
| 7,601,155 B2 | 10/2009 | Petersen | |
| 7,833,275 B2 | 11/2010 | Mears et al. | |
| 8,246,621 B2 | 8/2012 | Poncet | |
| 2003/0009170 A1 | 1/2003 | Tornier | |
| 2004/0122439 A1 | 6/2004 | Dwyer | |
| 2004/0236341 A1 | 11/2004 | Petersen | |
| 2014/0276866 A1 | 9/2014 | Endsley | |

FOREIGN PATENT DOCUMENTS

| | | |
|---|---|---|
| WO | WO2005/110250 | 11/2005 |
| WO | 2020/001832 A1 | 1/2020 |
| WO | 2020/002190 A1 | 1/2020 |
| WO | 2020/002198 A1 | 1/2020 |

OTHER PUBLICATIONS

WO International Search Report Application No. PCT/EP2019/066612, dated Oct. 1, 2019.

WO International Search Report Application No. PCT/EP 2019/060894, dated Aug. 9, 2019.

WO International Search Report Application No. PCT/EP2019/066596, dated Oct. 7, 2019.

* cited by examiner

SURGICAL KIT AND METHOD

CROSS-REFERENCE TO RELATED APPLICATIONS

This application is a National Stage Application filed Under 35 U.S.C. § 371 of International Application No. PCT/EP2019/060894 filed Apr. 29, 2019, which claims priority to GB1810480.2 flied Jun. 26, 2018 and GB1904257.1 filed Mar. 27, 2019, all of which are hereby incorporated by reference in their entireties.

FIELD OF THE INVENTION

This invention relates to a surgical kit and method for performing a controlled resection of the neck of a femur during a hip replacement procedure.

BACKGROUND OF THE INVENTION

Hip replacement is a surgical procedure in which the hip joint is replaced by a prosthetic implant. Total replacement of the hip joint involves installing an acetabular cup implant in the acetabulum of a patient and installing another implant in the femur of the patient. In partial hip replacement, an implant is installed in the femur of the patient, but an acetabular cup is not installed in the acetabulum. In either type of procedure, the implant that is installed in the femur typically includes a stem, which is received in the intramedullary canal, and a head having a bearing surface which is received in the acetabulum or acetabular cup implant. The implant typically also includes a neck, which extends between a proximal end of the stem and the head.

In a conventional procedure, in order to install the implant in the intramedullary canal, the neck of the femur is first resected. The resection of the femoral neck provides access to the intramedullary canal, which can then be prepared to receive the stem of the implant using broaches and reamers. During a hip replacement procedure, restoration of leg length is generally a product of good planning and experience and may generally be controlled by pre-operative planning. The neck resection may generally be a freehand cut and. A seating position of the implant, once the stem has been installed within intramedullary canal, may generally depend upon the location of the cut. If the cut is not correctly positioned, this can lead to an incorrect seating position for the implant. This can in turn adversely affect the resulting leg length of the femur with its femoral implant.

U.S. Pat. No. 6,503,255 B1 describes a cutting guide instrument and method for enabling high-precision resection of the head of the neck of a human femur at a predetermined cutting angle to the femoral shaft and on a predetermined cutting level with respect to the proximal end of the caput. A support part is fixed to the femur during the resection. A longitudinal guide carrier is supported by the support part and is aligned along the femoral collum at said predetermined cutting angle to the femoral shaft. A cutting guide is supported by and movable along the axis of the guide carrier to a cutting position corresponding to the predetermined cutting level.

WO 2002/026145 A1 describes a guiding instrument for the resection of a femoral neck in connection with total hip replacement, said guiding instrument comprising an instrument body having means for receiving a shank or the like that is mounted in the medullary canal of the femoral neck, said shank having a longitudinal centre axis the instrument body being displacable along said shank, and a guiding means having a guiding arrangement for the means that perform cutting of the femoral neck. At least a rotation ruler is attached to the instrument body, said rotation ruler being intended to cooperate with the existing femoral head of the femur.

U.S. Pat. No. 5,578,037 A describes a surgical resection guide that enables a surgeon to resect a femoral neck, during a hip arthroplasty procedure, such that a femoral prosthesis can be implanted within a patient to preserve or closely approximate the anatomic center of rotation of the hip. The guide is able to be used for left or right hip arthroplasty procedures, with either anterior or posterior surgical approaches.

U.S. Pat. No. 8,246,621 B2 describes an instrument kit is provided for reaming bone around a head of a bone, the bone including an implanted epiphysis component. The instrument kit includes a reaming guide and a reamer. The reaming guide is couplable to the epiphysis component and has a first reamer support feature and a second reamer support feature. The reamer is couplable to one of the first reamer support feature and the second support feature to ream bone around the epiphysis component.

U.S. Pat. No. 7,601,155 B2 describes an intramedullary femoral broach that aligns two instruments. A femoral neck resector guide slides over the broach and centers on the patient's femoral head to determine the height and angular rotation of resection. A circular ring of the head and cutting anus assure the system will fit any femur. A template is applied to the femoral broach and seats itself against the buttress of the broach locking it into place. The broach is then reinserted into the intramedullary canal. When the template reaches the greater trochanter the sizer is adjusted to the rotational anteversion of the canal. The handle of the femoral broach is struck with a mallet until the template is imbedded into the proximal femoral neck intramedullary bone. A retractor facilitates reaming of the acetabulum through a small anterior incision. A proximal portion digs into the bone of the superior acetabulum to allow for retraction of soft tissues.

U.S. Pat. No. 4,959,066 A describes an osteotomy guide assembly for femoral neck osteotomy includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with the saddle locator assembly. The saw guide is attached to the support bar by a single locking means which provides for positional adjustment of the saw guide relative to the support bar in two directions, including adjustment in the anterior-posterior direction along the transverse support bar and axially along the femur via a post which extends from the saw guide.

U.S. Pat. No. 7,833,275 B2 describes a method and apparatus for performing a minimally invasive total hip arthroplasty. An approximately 3.75-5 centimeter (1.5-2 inch) anterior incision is made in line with the femoral neck. The femoral neck is severed from the femoral shaft and removed through the anterior incision. The acetabulum is prepared for receiving an acetabular cup through the anterior incision, and the acetabular cup is placed into the acetabulum through the anterior incision. A posterior incision of approximately 2-3 centimetres (0.8-1.2 inches) is generally aligned with the axis of the femoral shaft and provides access to the femoral shaft. Preparation of the femoral shaft including the reaming and rasping thereof is performed through the posterior incision, and the femoral stem is inserted through the posterior incision for implantation in the femur. A variety of novel instruments including an osteotomy guide; an awl for locating a posterior incision aligned with the axis of the femoral shaft; a tubular posterior retractor; a selectively lockable rasp handle with an engagement guide; and a selectively lockable provisional neck are utilized to perform the total hip arthroplasty.

U.S. Pat. No. 5,607,431 A describes a surgical instrument system for preparing the medullary canal of the femur for implanting a prosthetic femoral component includes a template to be used in determining osteotomy position from an x-ray. A gauge is provided to locate and mark this position on the anterior femur. A distal reamer having an elongated drive shaft is used to form the canal to receive the distal stem of the femoral component. A metaphyseal template is used to determine the proper anteversion/retroversion and a chisel is used to cut the lateral area of the femur, both of which are guided by the elongated reamer shaft. A proximal broach also guided by the reamer shaft is used to shape the proximal medullary canal.

U.S. Pat. No. 7,582,091 B2 describes an osteotomy guide for indicating the femoral neck resection on a femur and its method of use are presented. The osteotomy guide includes an indexing feature for aligning the guide with an anatomic landmark and a resection guide for indicating the resection relative to the indexing feature.

U.S. Pat. No. 4,621,630 A describes a guide for femoral neck osteotomy that comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongate planar surface disposed at an angle of 45 DEG to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongate planar surface of the guide bar whereby an instrument in engagement with that surface traverses the femoral neck at an angle of 45 DEG to the long shaft axis of the femur.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a surgical kit for performing a controlled resection of the neck of a femur during a hip replacement procedure, the surgical kit comprising:

a mounting portion, wherein the mounting portion includes at least two guide holes for inserting guide pins into the femoral head while the mounting portion is located on an anterior aspect of the femoral head;

a body portion connected to the mounting portion, wherein the body portion includes an opening for mounting the body portion on an intramedullary pin located in an intramedullary canal of the femur; and a resection guide including at least two guide holes having the same layout as the guide holes of the mounting portion, to allow the resection guide to be mounted on the anterior aspect of the femoral head with said guide pins inserted into the femoral head for positioning a resection plane indicator of the resection guide with respect to the neck of the femur.

A kit according to embodiments of this invention can aid in indicating a correct position of the neck resection plane, for restoring the leg length in a hip replacement procedure. Embodiments of this invention achieve this by providing a body portion that can be mounted on the femur using an intramedullary pin (such as an initiation rod or reamer) located in the intramedullary canal of the femur to create an extramedullary reference to the intramedullary axis and a mounting portion that can be used to reference the femoral head center while inserting guide pins into the femoral head, and a resection guide having corresponding guide holes for mounting the resection guide on the guide pins such the correct resection plane is then indicated on the neck of the femur at a position relative to the femoral head center.

The resection plane indicator can, for instance, indicate a position of two resection planes. This can allow a neck resection using two angled cuts to be implemented. The two resection planes can be oriented at an angle of about 127°, 129° or 135° with respect to each other.

The resection plane indicator can comprise a guide slot or a guide surface.

The guide slot or guide surface can be a cutting slot or a cutting guide surface for receiving a blade of a cutting device during said resection of the neck.

The resection guide can include a plurality of sets of guide holes. Each set of guide holes can include at least two guide holes having the same layout as the guide holes of the mounting portion. The plurality of sets of guide holes can be respectively positioned in the resection guide to allow adjustment of the position of the resection plane indicator with respect to the neck of the femur by mounting the resection guide on the anterior aspect of the femoral head with the guide pins inserted into the guide holes of one of the sets of guide holes.

The mounting portion can include three guide holes. This can provide additional stability/accuracy in the mounting of the mounting portion and subsequently the resection guide.

The guide holes of the mounting portion can comprise:

a central guide hole for alignment with the femoral head center when the mounting portion is located on the anterior aspect of the femoral head; and a lateral guide hole located on a first side of the central guide hole; and a medial guide hole located on a second side of the central guide hole opposite the first side.

The surgical kit can further include a plurality of the guide pins.

The opening for mounting the body portion on the intramedullary pin can be adjustably positionable within the body portion according to a femoral offset of the femur.

The body portion can include markings for reading off the femoral offset of the femur according to the position of the opening for mounting the body portion on the intramedullary pin, while the mounting portion is mounted on the femoral head. The femoral offset value that is read off can be used to determine the type of neck/head combination that is used in the implant, for restoring the femoral offset.

The kit can include a plurality of the resection guides, each resection guide being of a different shape and/or size according to a respective implant geometry, for a positioning a resection plane indicator of a selected resection guide with respect to the neck of the femur. The implant geometries may, for instance, include standard, lateralised, short neck and/or, coxa vara geometries.

The mounting portion may include a substantially circular femoral head contacting surface.

The mounting portion may be referred to by those skilled in the art as a spherometer.

According to another aspect of the invention, there is provided a method for performing a controlled resection of the neck of a femur during a hip replacement procedure using a surgical kit comprising:

a mounting portion, wherein the mounting portion includes at least two guide holes for receiving pins;

a body portion connected to the mounting portion, the body portion having an opening; and a resection guide, wherein the resection guide includes at least two guide holes having the same layout as the guide holes of the mounting portion, the method comprising:

mounting the body portion on an intramedullary pin located in an intramedullary canal of the femur by inserting the pin into the opening in the body portion;

placing the mounting portion on an anterior aspect of the femoral head;

inserting a respective guide pin through each guide hole of the mounting portion and into the femoral head;

removing the mounting portion from the femoral head;

mounting the resection guide on the anterior aspect of the femoral head with said guide pins inserted into the femoral head for positioning a resection plane indicator of the resection guide; and using the resection plane indicator to either:

mark the position of the resection plane on the neck of the femur; or guide a blade of a cutting device to resect the neck of the femur.

A method according to embodiments of this invention can aid in indicating a correct position of the neck resection plane, for restoring the leg length in a hip replacement procedure. Embodiments of this invention achieve this by using a body portion that can be mounted on the femur using an intramedullary pin (such as an initiation rod or reamer) located in the intramedullary canal of the femur to create an extramedullary reference to the intramedullary axis, using a mounting portion to reference the femoral head center while inserting guide pins into the femoral head, and using a resection guide having corresponding guide holes for mounting the resection guide on the guide pins such the correct resection plane is then indicated on the neck of the femur at a position relative to the femoral head center.

The resection guide can include a plurality of sets of guide holes. Each set of guide holes can include at least two guide holes having the same layout as the guide holes of the mounting portion. The plurality of sets of guide holes can be respectively positioned in the resection guide to allow adjustment of the position of the resection plane indicator with respect to the neck of the femur by mounting the resection guide on the anterior aspect of the femoral head with said guide pins inserted into the guide holes of one of said sets of guide holes. The method can include:

selecting a set of guide holes; and mounting the resection guide on the anterior aspect of the femoral head with said guide pins inserted into the guide holes of one of the selected set of guide holes.

The method can include adjustably positioning the opening for mounting the body portion on the intramedullary pin with respect to a remainder of the body portion according to a femoral offset of the femur.

The method can include reading off the femoral offset of the femur according to the position of the opening for mounting the body portion on the intramedullary pin with respect to the remainder of the body portion according to a femoral offset of the femur, while the mounting portion is mounted on the femoral head.

The method can include using the femoral offset value to determine a femoral offset of a femoral implant to be installed in the hip replacement procedure.

The kit can include a plurality of the resection guides, each resection guide being of a different shape and/or size according to a respective implant geometry, for a positioning a resection plane indicator of a selected resection guide with respect to the neck of the femur. The method can further comprise: selecting one of the resection guides; and mounting the selected resection guide on the anterior aspect of the femoral head with said guide pins inserted into the femoral head. The implant geometries may, for instance, include standard, lateralised, short neck and/or, coxa vara geometries.

The method can include inserting the intramedullary pin into the intramedullary canal of the femur prior to mounting the body portion on the intramedullary pin.

The mounting portion may include a substantially circular femoral head contacting surface.

The mounting portion may be referred to by those skilled in the art as a spherometer.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

FIGS. 1A, 1B, 1C and 2 show the components of a kit 10 for performing a controlled resection of the neck of a femur 60 during a hip replacement procedure. As shown in the Figures, the various parts of the kit can, during the hip replacement procedure, be mounted on the femur 60, for determining one or more resection planes.

The kit 10 includes a mounting portion 310. The mounting portion 310 may be referred to by those skilled in the art as a spherometer. The mounting portion 310 can be mounted on an anterior aspect of the femoral head 62. The mounting portion 310 includes a femur facing surface. The mounting portion 310 may include a substantially circular femoral head contacting surface. The femur facing surface may be substantially concave and curved so as to fit against the femoral head 62. A rim of the femur facing surface may be substantially circular, for resting against the femoral head 62. In the present embodiment, the femur facing surface comprises a ring 320, which forms a substantially circular femoral head contacting surface, which can rest against the femoral head, as shown in the Figures.

During the hip replacement procedure, the surgeon may mount the mounting portion 310 on the anterior aspect of the femoral head 62 such that a central axis of the mounting portion 310 (e.g. see the dotted arrow labelled A in FIG. 1A) is aligned with the femoral head center 312 when viewing the femoral head 62 from an anterior position. This may generally be achieved by visual inspection of the anterior aspect of the femur 60 and femoral head 62 while manually positioning the mounting portion 310.

Figure 1A:
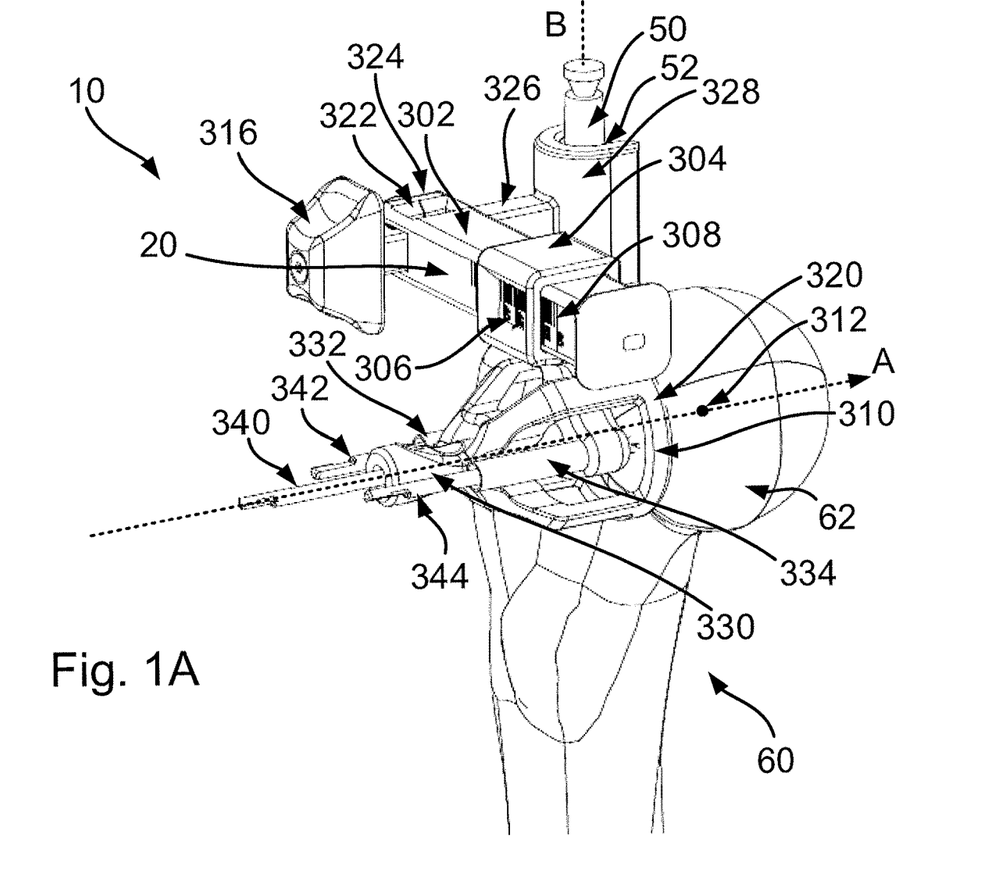
FIG. 1A shows a device mounted on the proximal end of a femur according to an embodiment of this invention.

The mounting portion 310 includes at least two guide holes. The guides holes extend through the mounting portion 310 to allow guide pins 340, 342, 344 of the kit 10 to be inserted into the femoral head while the mounting portion 310 is located on the anterior aspect of the femoral head 62 as shown in FIG. 1A. The distal ends of the guide pins 340, 342, 344 of the kit 10 may be sharpened, may be fluted, or may be otherwise configured to ease their insertion into the femoral head 62.

In the present embodiment, there are three guide holes, although it is envisaged that two guide holes of more than three guide holes could also be provided. For instance, the central guide hole of the present embodiment could be omitted so that just the lateral and medial guide holes are present. The guide holes in the present embodiment are provided in respective substantially cylindrical members 330, 320, 334. The substantially cylindrical members 330, 320, 334 in the present embodiment may be connected to the ring 320, so that their position relative to the ring 320 is fixed.

The three guide holes in the present embodiment include a central guide hole, a lateral guide hole located on a first side of the central guide hole and a medial guide hole located on a second side of the central guide hole opposite the first side. The central guide hole passes though the cylinder 330, the lateral guide hole passes though the cylinder 332, and the medial guide hole passes though the cylinder 334. The central guide pin 340 can be inserted into the central guide hole, the lateral guide pin 342 can be inserted into the lateral guide hole, and the medial guide pin 344 can be inserted into the medial guide hole.

The central guide hole extends along the central axis of the mounting portion 310 so that once the mounting portion 310 is mounted on the anterior aspect of the femoral head 62 as explained above, the central guide pin 340 can be inserted into the femoral head 62 along central axis of the mounting portion 310. Once inserted, the central guide pin thus points directly at the femoral head center 312. Similarly, once the mounting portion 310 is mounted on the anterior aspect of the femoral head 62 as explained above, the lateral guide pin 342 and medial guide pin 344 can be inserted through their respective guide holes and into the femoral head 62. The long axes of the guide holes are generally parallel to each other, to allow the resection guide 200 of the kit 10 subsequently to be mounted onto the guide pins as will be explained in more detail below.

The kit 10 may also include a body portion 20 connected to the mounting portion 310. The body portion can assist in the correct positioning of the mounting portion 310 on the femoral head 62 and can also allow measurements of the femoral offset to be taken. Further details regarding the body portion 20 will be provided below.

Once the guide pins 340, 342, 344 have been inserted into the femoral head 62, the mounting portion 310 (and the body portion 20) may be removed from the femur 60.

Figure 1B:
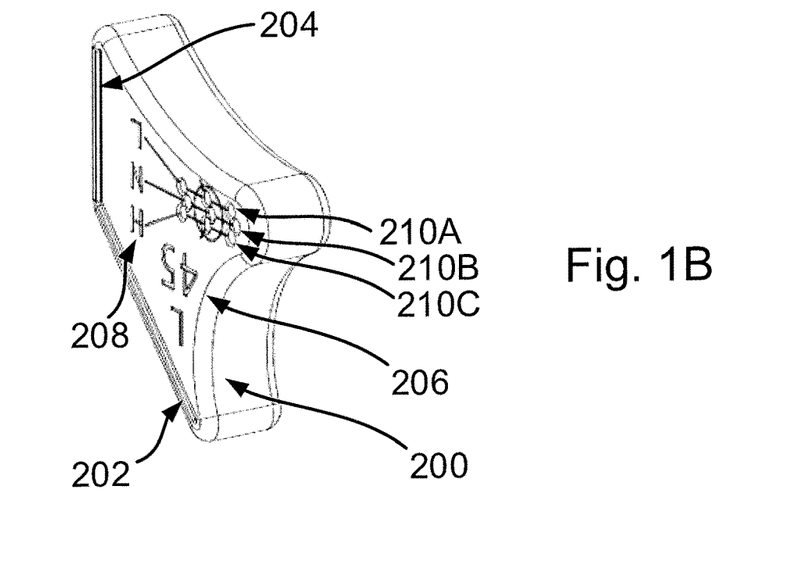
FIG. 1B shows a resection guide according to an embodiment of this invention.
Figure 1C:
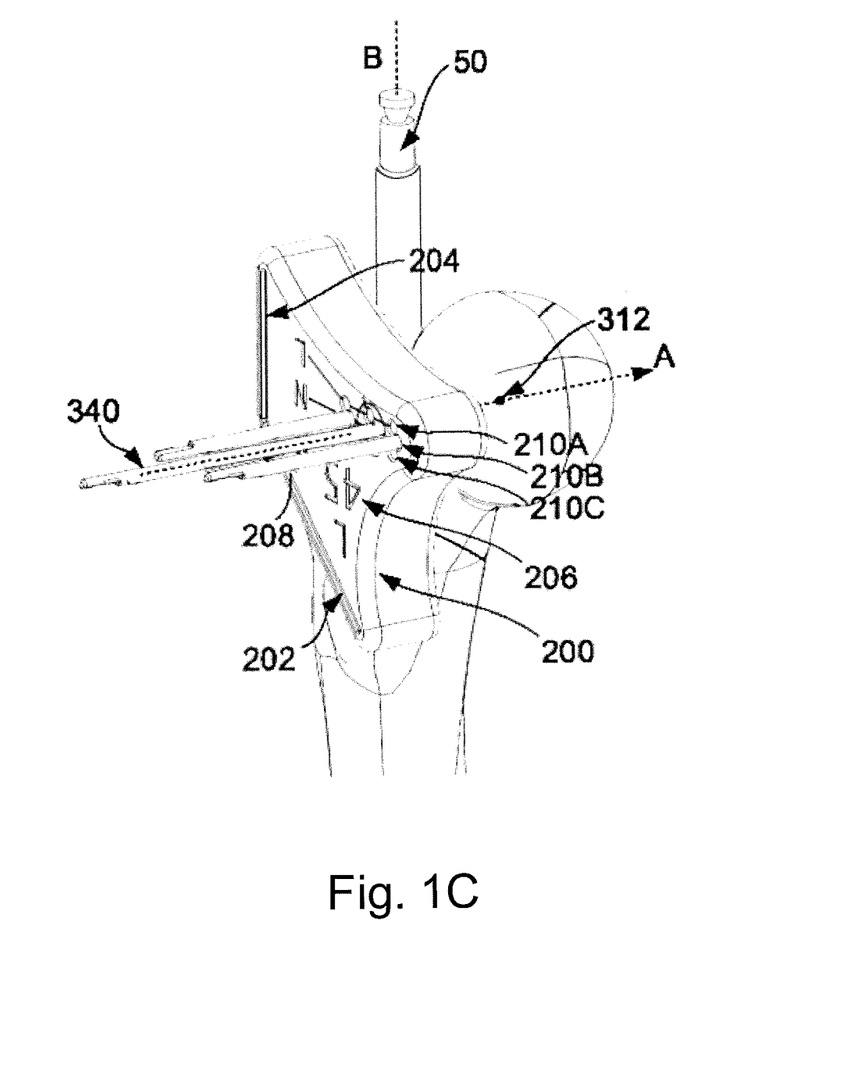
FIG. 1C the resection guide of FIG. 1B mounted on the proximal end of a femur according to an embodiment of this invention.

The kit 10 also includes a resection guide 200 (see FIG. 1B). The resection guide 200 is a separate component of the kit 10, which can be used to indicate the position of the one or more resection planes.

Figure 5:
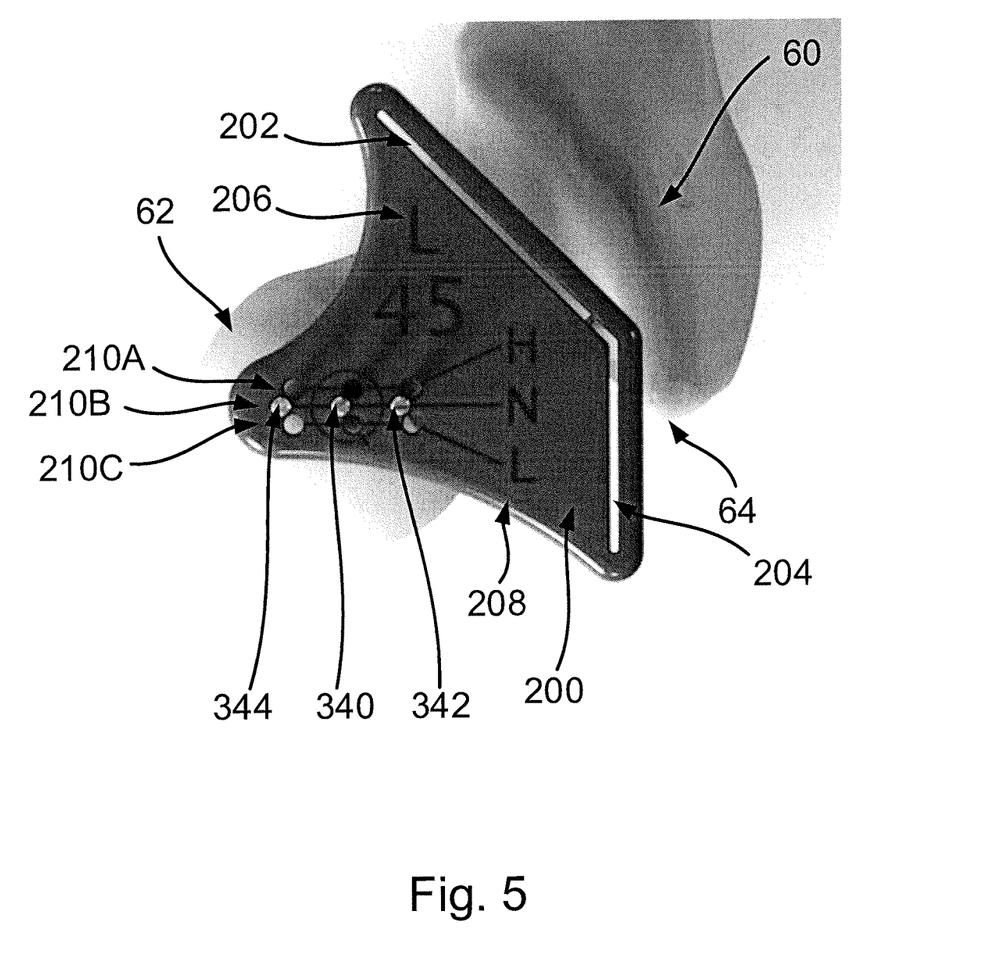
FIG. 5 shows an anterior view of a resection jig mounted on the anterior aspect of the head of a femur.

The resection guide 200 includes at least two guide holes 210. The guide holes 210 of the resection guide 200 have the same layout as the guide holes of the mounting portion 310. This can allow the resection guide 200 to be mounted on the guide pins (in this embodiment the guide pins 340, 342, 344) that have been inserted into the femoral head using the mounting portion 310, as shown in FIG. 5. Accordingly, using the guide pins 340, 342, 344, the resection guide 200 can be mounted on the anterior aspect of the femoral head 62 in a predetermined position relative to the femoral head center 312 (see FIG. 1C).

In the present embodiment, the resection guide 200 includes plurality of sets 210A, 210B, 210C of guide holes. Each set of guide holes 210A, 210B, 210C has a plurality of guide holes having a layout that matches the layout of the guide holes of the mounting portion 310, to allow the resection guide 200 to be mounted on the guide pins as explained above, using the guide holes of that set. The purpose of these sets 210A, 210B, 210C of guide holes will be explained below. However, it is envisaged that some embodiments may not include more than one set of guide holes. For instance, the sets of guide holes 210A and 210C may be omitted, such that the resection guide 200 shown in the Figures just includes guide holes that correspond to the set of guide holes 210B.

The resection guide 200 includes a resection plane indicator. The resection plane indicator indicates the position of one or more resection planes for resecting the femoral neck. With the resection guide 200 mounted on the guide pins 340, 342, 344 as described above, the resection plane indicator of the resection guide 200 is positioned in a predetermined location relative to the femoral head center 62. This can allow the resection plane(s) for resecting the femoral neck to be determined in a controlled fashion.

In the present embodiment, the resection plane indicator of the resection guide 200 comprises a guide slot 202/204. A first part 202 of the guide slot indicates a first resection plane, and a second part 204 of the guide slot indicates a second resection plane. The second resection plane (corresponding to the second part 204 of the guide slot), when viewed from an anterior position of the femur 60, may extend substantially parallel to the intramedullary axis of the femur 60 (which is indicated in, e.g., FIG. 2 using the dotted line labelled B). The first resection plane (corresponding to the first part 202 of the guide slot) extends at an angle $\theta$ with respect to the second resection plane. The angle $\theta$ may, for instance, be around 127°, 129° or 135°. Although the resection plane indicator in the present embodiment indicates two resection planes, it is envisaged that the resection plane indicator may indicate a single resection plane (e.g. the resection plane corresponding to the first part 202 of the guide slot).

The resection plane indicator may alternatively comprise a guide surface. For instance a peripheral edge of the resection plane indicator may include one or more substantially flat surfaces (e.g. surfaces such as the surfaces 203, 205 shown in FIG. 2) for indicating the resection planes.

The guide slot 202/204 (or the guide surface) may be used to mark the resection planes using a pen or scribe or such like. The guide slot 202/204 (or the guide surface) may also be used as a cutting slot or a cutting guide surface for receiving a blade of a cutting device during resection of the neck of the femur 60.

Figure 2:
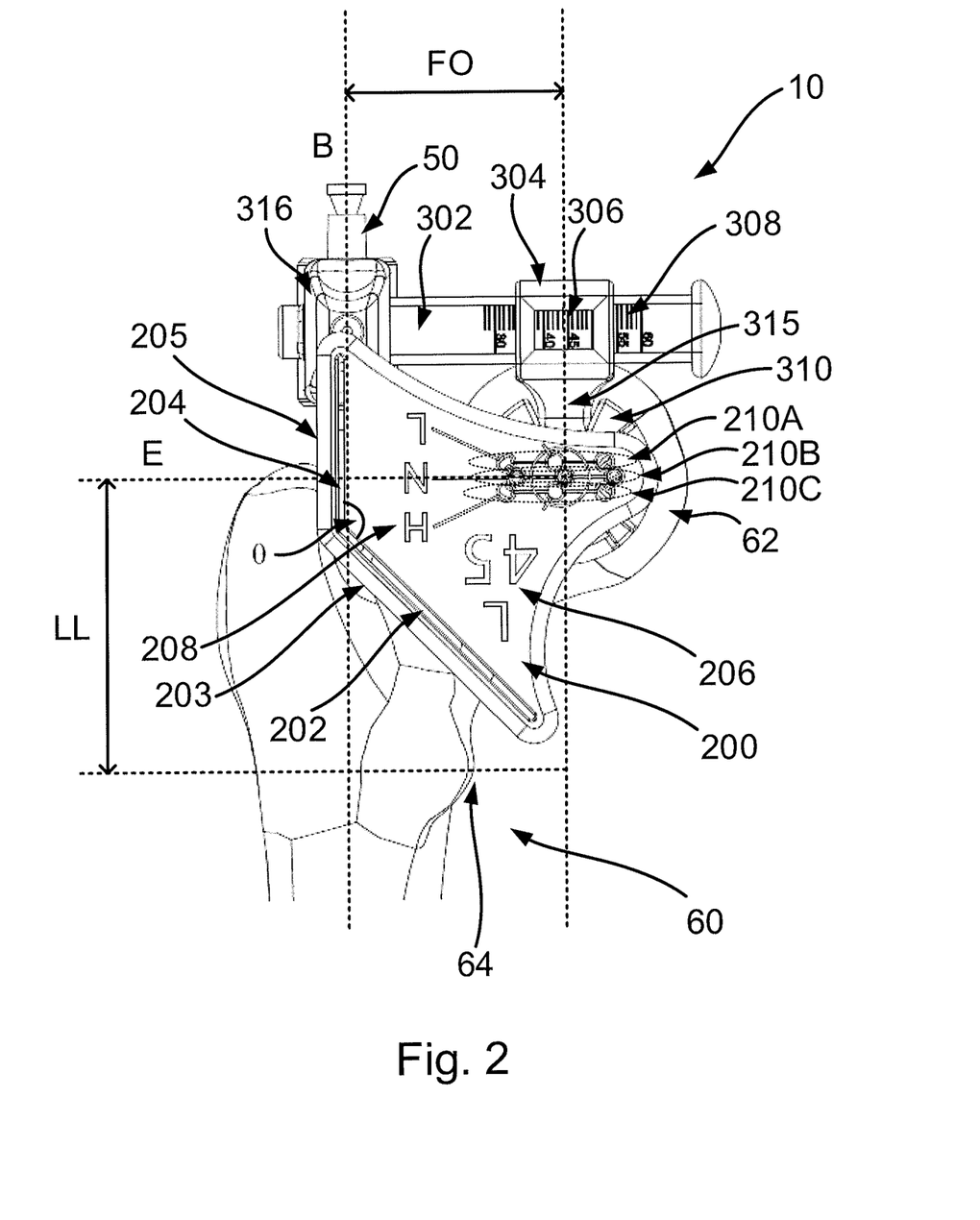
FIG. 2 shows an anterior view of the device of FIG. 1A mounted on a femur and the resection guide of FIG. 1B (FIG. 2 shows both the device of FIG. 1A and the resection guide of FIG. 1B in order to demonstrate the alignment of the their respective features with the anatomical feature of the femur, however it will be understood from the description of, for instance, FIGS. 1A to 1C that the device of FIG. 1A and the resection guide of FIG. 1B would not normally be mounted on the femur at the same time)

With reference to FIG. 2, for the purpose of this disclosure, the leg length (LL) of the femur 60 may be defined as the distance between the lesser trochanter 64 and the femoral head center, along a direction parallel to the intramedullary axis B. Again with reference to FIG. 2, for the purpose of this disclosure, the femoral offset of the femur 60 may be defined as the distance between the femoral head center and the intramedullary axis B, in a direction perpendicular to the intramedullary axis B.

The resection plane indicator can accordingly be positioned using the femoral head center 312 as a reference. In this way, the location of the resection plane(s) can be determined in a controlled manner. This in turn means that the seating position of the implant, once the stem of the implant has been installed within intramedullary canal, may be controlled. This can facilitate restoration of the leg length and/or femoral offset of the resulting femur 60 with its femoral implant particularly, but not necessarily exclusively, when using an implant system in which the neck length of the implant is constant. The kit 10 can include a plurality of differently shaped and/or sized resection guides 200. Each resection guide 200 can be used according to the implant geometry that is to be used during the hip replacement procedure. The implant geometries may, for instance, include standard, lateralised, short neck and/or, coxa vara geometries.

The resection guide 200 may include features for making fine adjustments to the position of the resection plane indicator relative to the femoral head center 62. For instance, as noted above, in the present embodiment, the resection guide 200 includes a plurality of sets 210A, 210B, 210C of guide holes. The set 210B of guide holes in this embodiment may be used for normal, unadjusted mounting of the resection guide 200, for positioning the resection plane indicator relative to the femoral head center 62. The set 210A of guide holes are positioned such that when the resection guide 200 is mounted on the guide pins 340, 342, 344 using that set, the resection plane indicator is positioned at a slightly lower position on the femur 60, for indicating a lower resection of the femur 60. As the position of the resection of the femoral neck dictates the seating position of the implant, this can in turn allow a slightly lower seating position to be chosen by the surgeon. One the other hand, the set 210B of guide holes are positioned such that when the resection guide 200 is mounted on the guide pins 340, 342, 344 using that set, the resection plane indicator is positioned at a slightly higher position on the femur 60, for indicating a higher resection of the femur 60. Again, as the position of the resection of the femoral neck dictates the seating position of the implant, this can in turn allow a slightly higher seating position to be chosen by the surgeon. In some embodiments, visual indicators 208 (e.g. L for low, N for normal and H for higher) may be provided on the resection guide, for reference by the surgeon. It is envisaged that any combination of sets of guide holes may be provided on the resection guide 200. For instance, the sets may include a first set for "normal", unadjusted mounting of the resection guide 200 on the guide pins 340, 342, 344, plus zero or more "high" sets, plus zero or more "low" sets.

As mentioned previously, the mounting portion 310 may be connected to a body portion 20. The body portion 20 can assist in the correct positioning of the mounting portion 310 on the femoral head 62 and can also allow measurements of the femoral offset to be taken.

The body portion 20 includes an opening 52 for mounting the body portion 20 on an intramedullary pin 50 located in an intramedullary canal of the femur 60. The intramedullary pin 50 can, for instance, comprise an initiation rod or reamer. The intramedullary pin 50 can be inserted into the intramedullary canal prior to mounting the body portion 20 and mounting portion 310 on the femur 60, so as to provide an extramedullary reference to the intramedullary axis B. The mounting of the body portion 20 in this way can aid in placing the guide pins 340, 342, 344 correctly by providing a reference to the intramedullary axis B and by providing additional stability for keeping the mounting portion 310 and body portion 20 in position, e.g. while inserting the guide pins 340, 342, 344 (and/or while taking the readings described below). The opening 52 may, for instance, comprise an aperture that passes through the body portion 20. Alternatively, the opening 52 may comprise a recess on the body portion, within which the intramedullary pin 50 may be received.

The position of the opening 52 may be adjustably positionable within the body portion 20, according to the femoral offset of the femur 60. This can allow the body portion to be adjusted so that it fits correctly on the intramedullary pin 50 with the mounting portion mounted on the anterior aspect of the femoral head 62 as described above. The body portion 20 may also include markings for reading off the femoral offset of the femur 60 according to the position of the opening 52 relative to the mounting portion 310, while the mounting portion 310 is mounted on the femoral head 62.

The body portion 20 in this embodiment includes a number of arms 315, 302, 326.

A first arm 315 connects the mounting portion 310 to the rest of the body portion. In this embodiment, when the mounting portion 310 is mounted on the femoral head 62 as described above, the first arm 315 extends in a direction substantially parallel to the intramedullary axis B.

The first arm 315 is connected to a second arm 302 of the body portion 20. The second arm 302 extends in a direction perpendicular to the first arm 315 such that, when the mounting portion 310 is mounted on the femoral head 62 as described above, the second arm 302 extends laterally with respect to the mounting portion 310, along a direction perpendicular to the intramedullary axis B and also perpendicular to the central axis of the mounting portion 310.

The body portion also includes a third arm 326. The third arm 326 is connected to the second arm 302 at a lateral position with respect to the mounting portion 310. The third arm 326 extends in a direction substantially parallel to the central axis of the mounting portion 310, such that when the mounting portion 310 is mounted on the femoral head 62 as described above, the third arm extends in a direction substantially perpendicular to the intramedullary axis B. The opening 52 may be provided in the third arm 326. In the present embodiment, the opening 52 is located at a posterior end of the third arm 326. The other end of the third arm 326 may include a handle 316, for manual positioning and adjustment of the third arm 326, e.g. when mount mounting the opening on the intramedullary pin 50.

The relative positions of the arms 315, 302, 326 may be adjustable, to allow the body portion 20 to be adjusted so that it fits correctly on the intramedullary pin 50 with the mounting portion 310 mounted on the anterior aspect of the femoral head 62 as described above.

In the present embodiment, the second arm 302 is slideably received within an aperture located at a superior end 304 of the first arm 315. This can allow the second arm 32 to be slid back and forth in a lateral/medial direction relative to the first arm 32. Similarly, the third arm 326 is slideably received within an aperture located at a lateral end 324 of the second arm 302. This can allow the third arm 326 to be slid back and forth in a posterior/anterior direction relative to the second arm 302.

Figure 3:
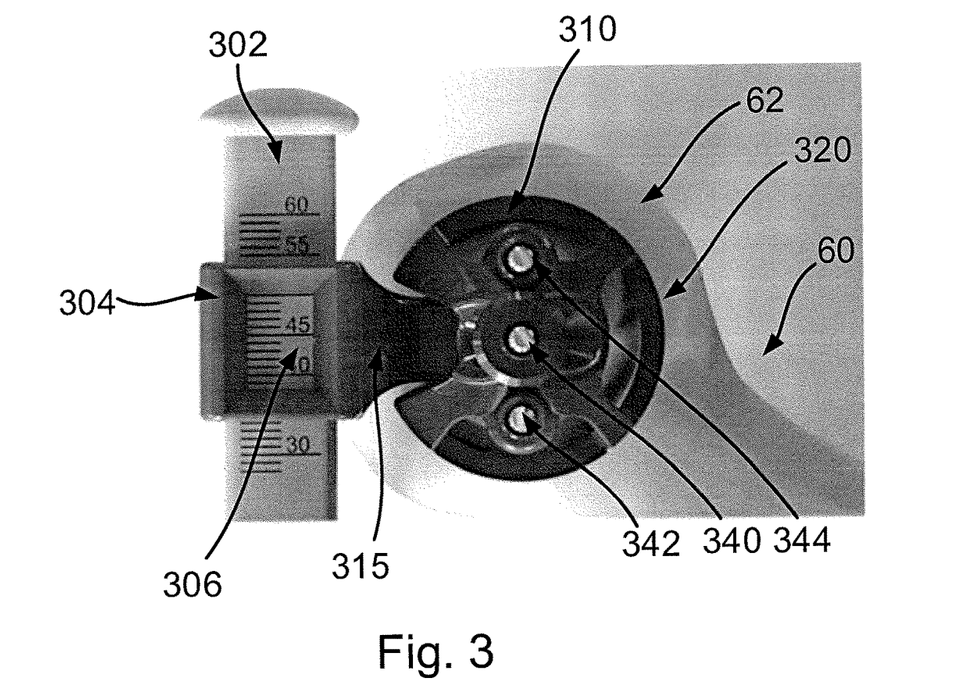
FIG. 3 shows an anterior view of the mounting portion of the device of FIG. 1 mounted on an anterior aspect of the head of a femur.

As shown in FIG. 3, the superior end 304 of the first arm 315 may include a window through which markings 306 located on the second arm 302 may be viewed. These markings 306 can be used to read off the femoral offset off the femur 60 when the mounting portion 310 and the body portion 20 are located on the femur 60 as described above.

Figure 4:
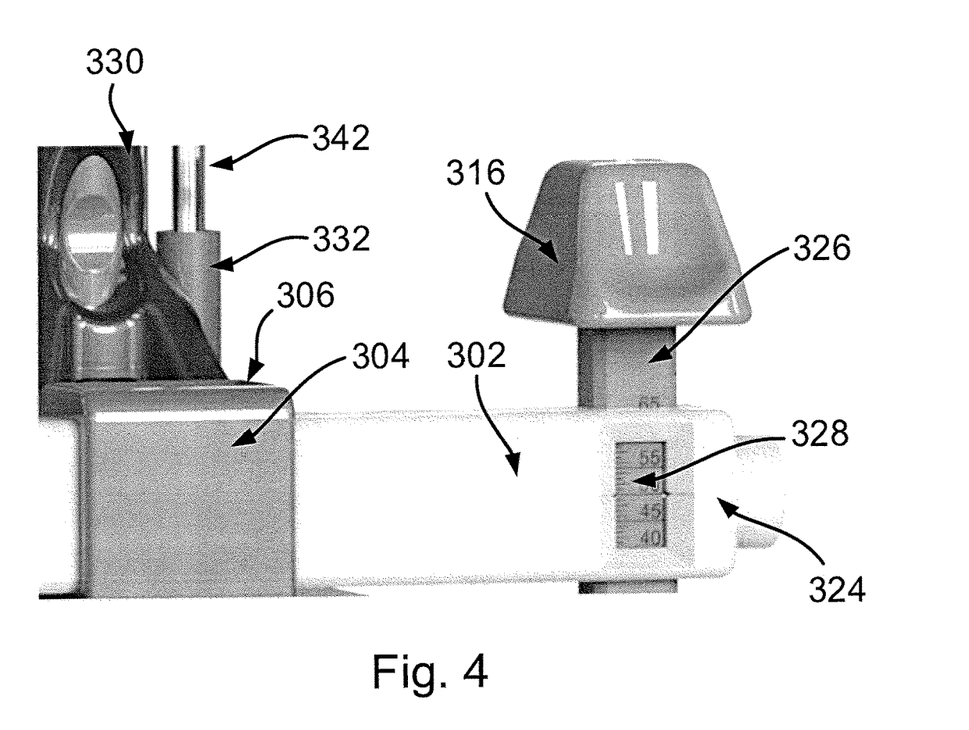
FIG. 4 shows a superior view of part of the device of FIG. 1 mounted on a femur.

As shown in FIG. 4, the lateral end 324 of the second arm 326 may include a window through which markings 328 located on the third arm 326 may be viewed. These markings 328 can be used to measure the antero-posterior offset and for an indication of native femoral version when the mounting portion 310 and the body portion are located on the femur 60 as described above.

The implant that is to be installed in the femur 60 may generally include a stem, which is to be received in the intramedullary canal, and a head having a bearing surface which is to be received in the acetabulum or acetabular cup implant. The implant may typically also includes a neck, which extends between a proximal end of the stem and the head. The stem and neck may be integrally formed. The head may be attachable to the end of the neck. The readings taken using the markings 306, as well as the size (diameter/radius) of the femoral head 62 can be used to inform the choice of head that is used, for restoring the femoral offset.

Accordingly, there has been described a surgical kit and method for performing a controlled resection of the neck of a femur during a hip replacement procedure. The kit includes a mounting portion. The mounting portion includes at least two guide holes for inserting guide pins into the femoral head while the mounting portion is located on an anterior aspect of the femoral head. The kit also includes a resection guide including at least two guide holes having the same layout as the guide holes of the mounting portion, to allow the resection guide to be mounted on the anterior aspect of the femoral head with the guide pins inserted into the femoral head for positioning a resection plane indicator of the resection guide with respect to the neck of the femur. The method also includes placing the mounting portion on an anterior aspect of the femoral head. The method further includes inserting a respective guide pin through each guide hole of the mounting portion and into the femoral head. The method also includes removing the mounting portion from the femoral head. The method further includes mounting the resection guide on the anterior aspect of the femoral head with said guide pins inserted into the femoral head for positioning a resection plane indicator of the resection guide. The method also includes using the resection plane indicator to either: mark the position of the resection plane on the neck of the femur; or guide a blade of a cutting device to resect the neck of the femur.

Although particular embodiments of the invention have been described, it will be appreciated that many modifications/additions and/or substitutions may be made within the scope of the claimed invention.

The invention claimed is:

1. A surgical kit for performing a controlled resection of the neck of a femur during a hip replacement procedure, the surgical kit comprising:
   a mounting portion comprising a substantially circular femoral head contact surface, wherein the mounting portion includes at least two guide holes extending therethrough in an anterior-posterior direction for inserting guide pins into the femoral head while the mounting portion is located on an anterior aspect of the femoral head, wherein the at least two guide holes comprises a central guide hole for alignment with the femoral head center when the mounting portion is located on the anterior aspect of the femoral head; and a lateral guide hole located on a first side of the central guide hole; and a medial guide hole located on a second side of the central guide hole opposite the first side;
   a body portion slidably coupled to the mounting portion, wherein the body portion includes an opening extending therethrough in a traversing direction to the anterior-posterior direction for mounting the body portion on an intramedullary pin located in an intramedullary canal of the femur, wherein the mounting portion is configured to slide along the body portion in a direction traversing the traversing direction of the opening and the anterior-posterior direction; and
   a resection guide including at least one resection plane indicator and at least two guide holes having the same layout as the at least two guide holes of the mounting portion, to allow the resection guide to be mounted on the anterior aspect of the femoral head with said guide pins inserted into the femoral head for positioning the at least one resection plane indicator of the resection guide with respect to the neck of the femur for guiding a blade of a cutting device during said resection of the neck.

2. The surgical kit of claim 1, wherein the at least one resection plane indicator indicates a position of two resection planes.

3. The surgical kit of claim 2, wherein the two resection planes are oriented an angle of about 127', 129' or 135' with respect to each other.

4. The surgical kit of claim 1, wherein the at least one resection plane indicator comprises a guide slot or a guide surface.

5. The surgical kit of claim 4, wherein the guide slot or the guide surface is a cutting slot or a cutting guide surface for receiving the blade of the cutting device during said resection of the neck.

6. The surgical kit of claim 1, wherein the resection guide includes a plurality of sets of guide holes, wherein each set of guide holes includes at least two guide holes of the at least two guide holes having, the same layout as the guide holes of the mounting portion, wherein the plurality of sets of guide holes are respectively positioned in the resection guide to allow adjustment of the position of the resection plane indicator with respect to the neck of the femur by mounting the resection guide on the anterior aspect of the femoral head with said guide pins inserted into the guide holes of one of said sets of guide holes.

7. The surgical kit of claim 1, further including a plurality of said guide pins.

8. The surgical kit of claim 1, wherein the opening for mounting the body portion on the intramedullary pin is adjustably positionable within the body portion according to a femoral offset of the femur.

9. The surgical kit of claim 8, wherein the body portion includes markings for reading off the femoral offset of the femur according to the position of the opening for mounting the body portion on the intramedullary pin, while the mounting portion is mounted on the femoral head.

10. The surgical kit of claim 1, wherein the kit includes a plurality of said resection guides, each resection guide being of a different shape and/or size according to a respective implant geometry, for a positioning a resection plane indicator of a selected resection guide with respect to the neck of the femur.

\* \* \* \* \*